United States Patent [19]

Smith

[11] Patent Number: 4,978,510

[45] Date of Patent: Dec. 18, 1990

[54] STERILIZING TRAY

[75] Inventor: Lawrence C. Smith, Sumner, Wash.

[73] Assignee: Pascal Company, Inc., Bellevue, Wash.

[21] Appl. No.: 220,267

[22] Filed: Jul. 18, 1988

[51] Int. Cl.$^5$ ............................ A61L 2/18; B65D 1/34
[52] U.S. Cl. .................................... 422/310; 422/297; 422/300; 206/438; 206/439; 206/560; 206/557; 206/559
[58] Field of Search .................... 422/297, 300, 310; 206/438, 439, 560, 557, 559

[56] References Cited

U.S. PATENT DOCUMENTS

| | | | |
|---|---|---|---|
| 553,561 | 1/1896 | Lundholm | 422/300 |
| 846,030 | 3/1907 | Hullhorst . | |
| 857,240 | 6/1907 | Henning . | |
| 2,786,245 | 3/1957 | Steinbock, Jr. | 422/310 |
| 3,902,595 | 9/1975 | Mori | 206/559 |
| 4,266,668 | 5/1981 | Paek | 206/557 |

FOREIGN PATENT DOCUMENTS 1911066 10/1970 Fed. Rep. of Germany ...... 206/259
2202554 8/1972 Fed. Rep. of Germany ...... 206/559

Primary Examiner—Robert J. Warden
Assistant Examiner—Abanti B. Singla
Attorney, Agent, or Firm—Gregory W. Moravan

[57] ABSTRACT

A sterilizing tray for holding objects while they are being sterilized in a sterilizing solution. At least one end of the sterilizing tray is equipped with a top pivoting end door whose latch can be released by tipping the end of the sterilizing tray against the work surface. Once the latch is released, the weight of sterilized objects in the tipped sterilizing tray pushes the end door open, thereby depositing the sterilized objects neatly on the work surface without their ever having been touched by the user.

9 Claims, 4 Drawing Sheets

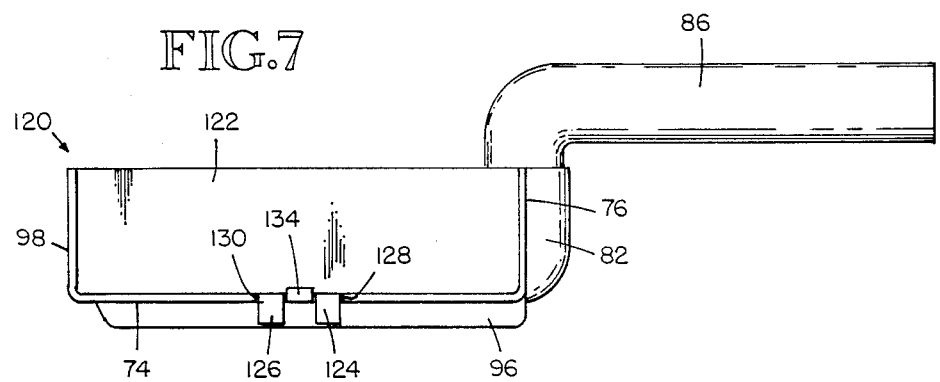
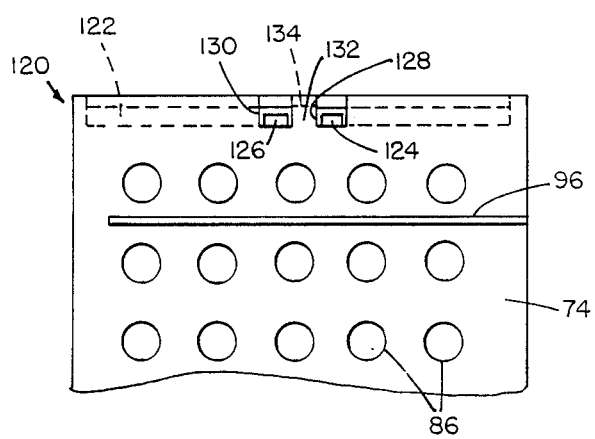

STERILIZING TRAY

BACKGROUND OF THE INVENTION

The present invention relates to sterilizing trays, and more particularly, it relates to a sterilizing tray having end doors which can be released without touching them.

SUMMARY OF THE INVENTION

Medical devices or things, such as dental instruments, must be sterilized after they have been used on a patient, in order to prevent the risk of cross infection between patients. For simplicity, only dentists and dental instruments will be referred to hereinafter, it being understood that the present invention can be used by anyone in sterilizing any kind of object—medical, dental or otherwise.

Such sterilizing is conventionally done in the dentist's office by first placing the instruments in a perforated tray or basket, and then immersing the instruments in a container of sterilizing solution for a period of time which is adequate to sterilize them. The instruments are then removed from the sterilizing solution and rinsed in hot water to wash away the sterilizing solution.

Next the instruments are dumped out of the tray or basket onto a clean towel, with which they are dried. However, if the user touches the instruments they may be contaminated, thereby requiring that they be resterilized. Further, such a dumping procedure often results in the instruments landing in a hard to deal with untidy, jumbled pile; and occasionally the instruments may even be scattered off of the clean towel or will drop to the floor, thereby requiring that they be resterilized.

Accordingly, one of the primary objects of the present invention is to provide a sterilizing tray which avoids all of these problems, by being equipped with at least one top pivoting end door which can be unlatched without the user ever touching it or the instruments in the sterilizing tray. If desired, such an end door can be provided at both ends of the sterilizing tray.

According to the present invention, the top portion of each end of the end door is provided with a pivot pin which is received in a corresponding, vertically elongated pivot slot in the side wall of the sterilizing tray. The end door is provided with a latch means having a release means which can be selectively actuated by tipping the end of the sterilizing tray against the work surface, thereby raising the end door a distance sufficient to unlatch it. Such raising of the end door is permitted by the vertically elongated pivot slots which are provided for the end door's pivot pins. Once the latch is released, the weight of the instruments within the tipped tray pushes the end door open, thereby neatly depositing the instruments on the work surface without the user ever having to touch them or the end door.

In one form of the invention the latch comprises a necked latching slot in the base of the tray which cooperates with a necked, dual purpose latching and release tab which extends downwardly from the bottom of the sterilizing tray's end door.

In another form of the invention, the latch comprises a latch arm having a latch tab which prevents the end door from opening until at least one release tab on the bottom of the door is actuated.

A safety ramp may be provided on the base of the sterilizing tray adjacent the end door to prevent the instruments from getting under the end door and accidentally releasing it.

A handle may be provided for the sterilizing tray which rotates in a socket in the center of one edge of the sterilizing tray. The handle may be provided with detent means to enable the handle to be releasably locked in an outwardly extending operating position, or in an inwardly extending stowed position. Even in its stowed position, the handle may be used to manipulate the sterilizing tray.

It is to be understood that the forgoing is intended to be a brief, not an exhaustive, summary of some of the objects, features, advantages and characteristics of the present invention. It is to be noted that these and further objects, features, advantages and characteristics of the present invention will be directly or indirectly disclosed to those skilled in the art to which it pertains by the following, more detailed description of the present invention.

BRIEF DESCRIPTION OF THE FIGURES

FIG. 7 is an end elevational view of the second form of the sterilizing tray; and FIG. 8 is a bottom elevational view of one end portion of the second form of the sterilizing tray.

DESCRIPTION OF THE PREFERRED EMBODIMENTS

Figure 1:
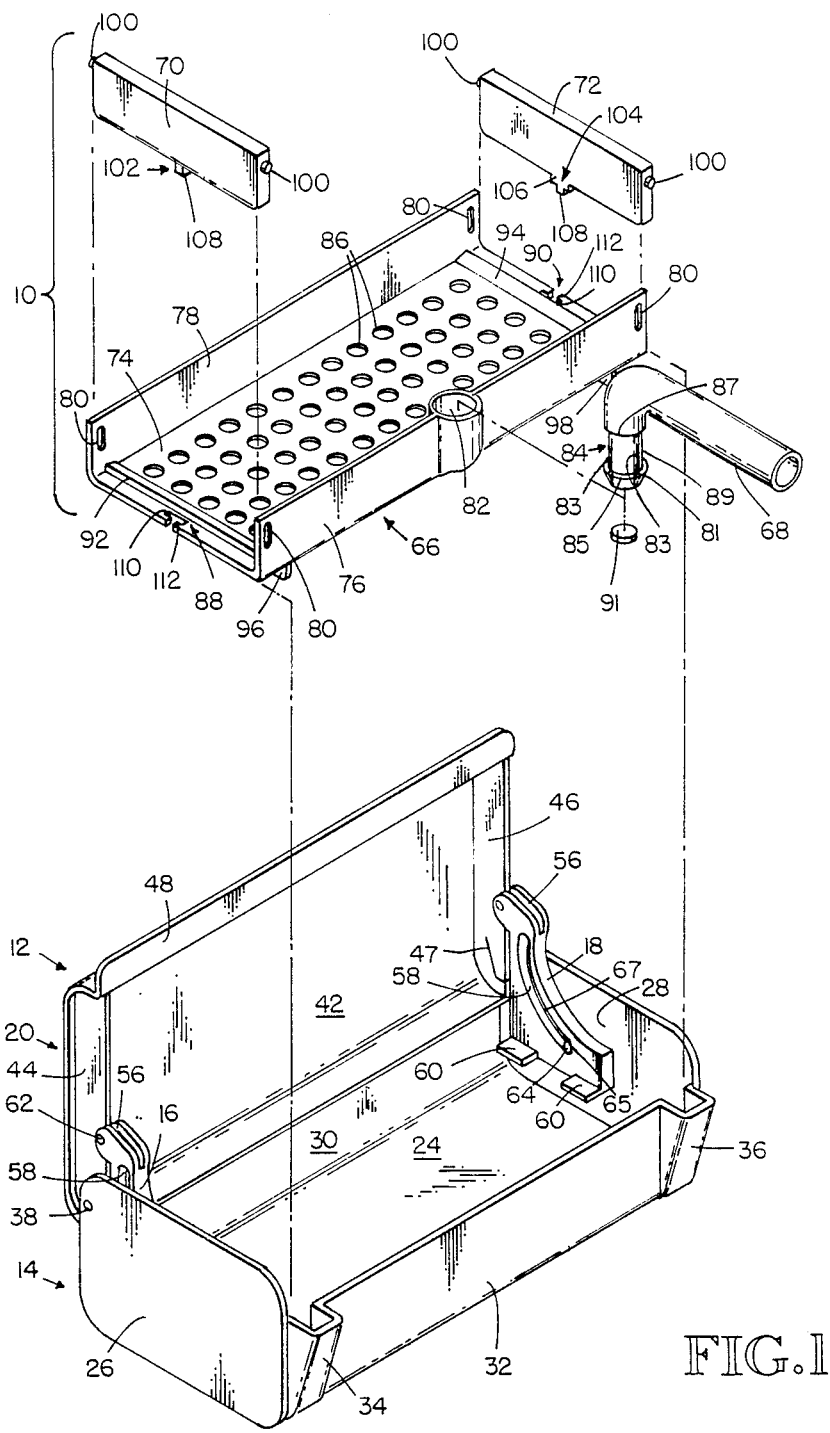
FIG. 1 is a partially exploded perspective view of a first form of the sterilizing tray of the present invention, wherein the sterilizing tray is shown exploded and wherein a sterilizing container used with the sterilizing tray is shown not exploded.

Turning now to FIG. 1, the sterilizing tray is shown generally designated at 10; while the sterilizing container is shown generally designated at 12.

Figure 2:
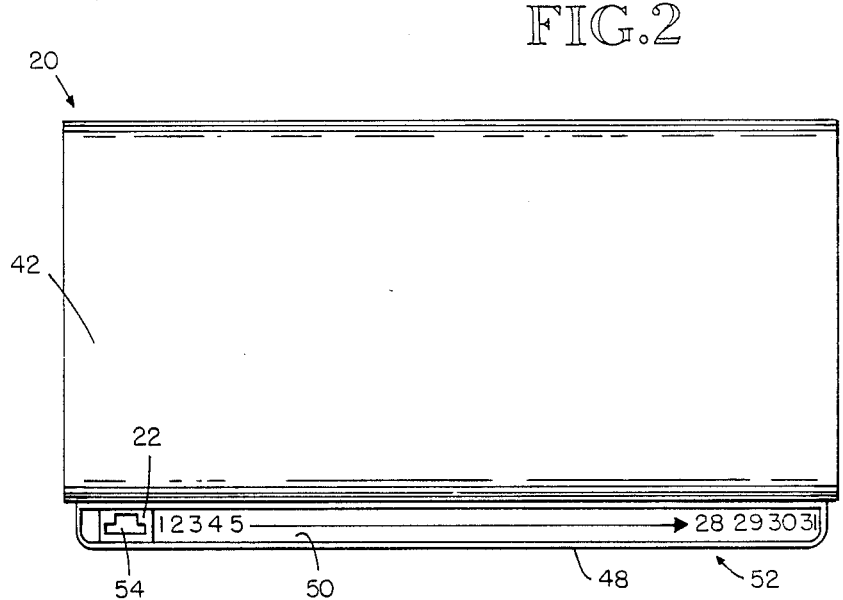
FIG. 2 is a top elevational view of the cover of the sterilizing container.

Referring now to FIGS. 1 and 2, the sterilizing container 12 comprises a base 14; a pair of tray arms 16, 18; a cover 20; and a date slide 22 (FIG. 2).

Base 14 has a bottom 24; a pair of side walls 26, 28; a back wall 30; and a front wall 32 having a pair of pour spouts 34, 36. Base 14 is watertight, so it can hold whatever sterilizing liquid which is used in the sterilizing container 12. Base pour spouts 34, 36 are used to help make the pouring of the sterilizing fluid from the sterilizing container 12 more convenient and neat, such as when the sterilizing fluid needs to be changed.

Cover 20 is rotatably mounted to base 14 by a pair of hinge pins 38. Cover 20 comprises top wall 42 and a pair of end walls 44, 46. Each hinge pin 38 is preferably molded as part of the outer face of its respective end wall 44, 46. A slot 47 is provided in each end wall 44, 46 near each hinge pin 38. The purpose of slots 47 is to permit the portion of each end wall 44, 46 which is near its respective hinge pin 38 to bow inwardly while hinge pins 38 are being positioned to be inserted into their respective bores in the side walls 26, 28 of base 14.

The cover's end walls 44, 46 are inset slightly from the ends of its top wall 42, as seen, so that when cover 20 is closed, the end portions of top wall 42 make a close contact with the corresponding top portions of base side walls 26, 28.

Such close contact not only helps to prevent any of the sterilizing fluid's fumes or odors from escaping from sterilizing container 12, but it also helps to keep foreign matter out of the sterilizing container 12 when cover 20 is closed.

For the same reason, when cover 20 is closed protruding lip 48 on the cover's top wall 42 makes a close contact with the corresponding top portions of base pour spouts 34, 36 and base front wall 32. The cover's protruding lip 48 is also used as a handle by which cover 20 may be conveniently opened and closed by the user.

Referring now to FIG. 2, it is seen that the top side of the cover's protruding lip 48 defines an elongated recess 50 which is slightly tapered in a vertical direction, i.e. the width of recess 50 at its bottom is slightly greater than its width at its top. In the bottom of recess 50 are date indicia 52 which comprise all of the numbers from one through thirty-one. Date indicia 52 may be molded in the bottom of recess 50 when cover 20 is made; or they may be printed on a piece of paper or plastic which is then glued to the bottom of recess 50. As seen, the date indicia 52 are offset from the left end of recess 50, to provide a non-dated portion of recess 50 into which date slide 22 may be positioned when date slide 22 is not being used to keep track of the date.

Date slide 22 has a width which is slightly greater than the width of the top of recess 50. Date slide 22 is slideably secured within recess 50 with a snap fit by simply urging date slide 22 downwardly into recess 50 until it snaps into place.

Referring again to FIG. 1, each tray arm 16, 18 has a cover slot 56, an arcuate guide slot 58, and a pair of support legs 60 which extend inwardly a short distance towards the center of base 14.

The upper end of each tray arm 16, 18 is pivotally connected by a pivot pin 62 to a respective cover end wall 26, 28, which extends into a respective tray arm cover slot 56, as seen. Each pivot pin 62 is preferably molded as part of the outer surface of its respective end wall 44, 46, and is received in a corresponding bore on tray arm 16, 18.

The arcuate guide slot 58 of each tray arm 16, 18 is sized to slideably receive a guide pin 64 which is preferably molded as part of the inner surface of its respective base end wall 26, 28. The free end of each guide pin 64 includes a small hook 65 that extends a short distance radially outwardly from the rest of guide pin 64, as seen in FIG. 1. An arcuate recess 67, which extends along the upper side of guide slot 58 is provided for hook 65, so that the top of hook 65 is recessed below the surface of its respective tray arm 16, 18. This prevents hook 65 from interfering with the insertion of sterilizing tray 10 into sterilizing container 12.

Before the upper ends of tray arms 16, 18 are mounted to their respective pivot pins 62, tray arms 16, 18 are mounted to their respective guide pins 64 by first orienting their guide slots 58 parallel to the hooks 65 on their respective guide pins 64. When so oriented, the tray arms 16 18 may then be passed down over their respective guide pins 64. Then, when tray arms 16, 18 are rotated on their guide pins 64 so that their upper ends may be mounted to their pivot pins 62, the hooks 65 on their respective guide pins 64 retain tray arms 16, 18 on their respective guide pins 64.

Each arcuate guide slot is also sized such that it acts as a stop, in cooperation with its respective guide pin 64, as seen in FIG. 1, to limit the travel of cover 20 when cover 20 is fully opened. The upper surface of the lower end of guide slot 58 includes a detent recess which cooperates with guide pin 64 to releaseably hold cover 20 in its fully open position, as seen in FIG. 1.

The various components of sterilizing container 12 are sized, shaped and located in such a manner that when cover 20 is opened and closed, tray arm legs 60 remain at least substantially horizontal.

All of the various components of sterilizing container 12 can be formed in any conventional way, such as by injection molding them from any suitable plastic which is non-toxic and which is compatible with whatever sterilizing liquid is placed in sterilizing container 12 during use. If it is desired that sterilizing container 12 also be able to withstand being sterilized in an autoclave, then the plastic must also, of course, be selected to be compatible with being autoclaved.

If it is inconvenient or impossible to injection mold any particular component of sterilizing container 12 in one piece, then that particular component may be molded as separate parts which are then secured together in any conventional way, such as by gluing, etc.

Turning now to FIGS. 1 and 3-5, it is seen that sterilizing tray 10 comprises a body 66, a tubular handle 68 and a pair of identical end doors 70, 72. Here again, all of the various components of sterilizing tray 10, can be formed in any conventional way, such as by injection molding them from any suitable plastic which is non-toxic, which is compatible with whatever sterilizing liquid is placed in sterilizing container 12 during use, and which is compatible with being autoclaved, if desired.

Tray body 66 comprises a base 74; and a pair of side walls 76, 78 which each define a pair of vertically elongated side wall pivot slots 80. A silicone rubber plug 91, which has an outer diameter greater than the inner diameter of the lower end 81 of tubular handle 68, is inserted inside lower end 81, where it is firmly retained in a compression fit.

Side wall 76 also defines a generally cylindrical socket 82. The half of the bottom of socket 82 which faces the center of tray 10 is open, for drainage and to assist in the molding process. The inner diameter of the upper portion of socket 82 is sized to receive the reduced outer diameter portion 89 of stub 84 of handle 68 in a snug, rotating fit. The lower end 81 of stub 84 is tapered, as seen, in order to help enable stub 84 to be inserted more easily into socket 82.

The lower portion of stub 84 of handle 68 is divided by four slots 83 into four equal fingers. Each finger has a locking barb 85. Slots 83 permit the lower ends of the four fingers, and their locking barbs 85, to be compressed inwardly slightly as stub 84 is inserted into socket 82, in order to permit locking barbs 85 to fit through the upper portion of socket 82. Stub 84 is also provided with an annular shoulder 87 which acts as a stop. When stub 84 is inserted into socket 82, its downward travel is limited by shoulder 87 contacting the top of socket 82.

Regarding the half of socket 82 which extends inwardly towards the center of tray 10, the inner diameter of the lower portion of said half of socket 82 is slightly larger than the inner diameter of the rest of socket 82, thereby forming a horizontal semicircular socket shoulder inside socket 82. When stub 84 of handle 68 is fully inserted into socket 82, at least one of the locking barbs 85 is fully opposite the slightly larger, lower portion of said half of socket 82. Thus, when said at least one locking barb 85 is so positioned, it is no longer compressed by socket 82, and so it moves outwardly slightly into the slightly larger, lower portion of said half of socket 82 under the urging of its own resiliency and under the urging of compressed silicone rubber plug 91. If an upward force is then exerted on handle 68, said at least one locking barb 85 engages the socket shoulder inside socket 82, thereby preventing stub 84 of handle 68 from being pulled out of socket 82.

Figure 3:
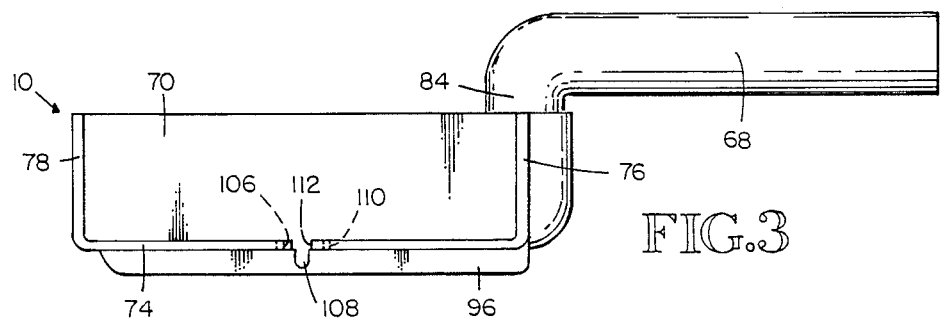
FIG. 3 is an end elevational view of the first form of the sterilizing tray.

As seen in FIG. 1, the four equally spaced slots 83 in stub 84 are oriented so that a plane extending through two of slots 83 is at a right angle with respect to the centerline of the horizontal portion of handle 68; while a plane passing through the other two slots 83 is oriented parallel to the centerline of the horizontal portion of handle 68. The vertical edges of locking barbs 85 which are located on the two slots 83 which are oriented at a right angle are relatively sharp. This is so said vertical edges can cooperate with the vertical edges of the slightly larger, lower portion of said half of socket 82, to act as detent means to releasably hold handle 68 in position when handle 68 is either extended directly outwardly from the center of tray 10, as seen in FIG. 3, or when it is extended directly inwardly towards the center of tray 10. On the other hand, the vertical edges of locking barbs 85 which are located on the two slots 83 which are oriented parallel to the centerline of the horizontal portion of handle 68 are quite rounded, so that they do not act as detent means in any position of handle 68.

Tray body base 74 defines a large number of drain holes 86 and a pair of necked slots 88, 90. Tray body base 74 also includes a pair of upwardly projecting end ramps 92, 94 and a pair of downwardly projecting legs 96, 98.

Figure 4:
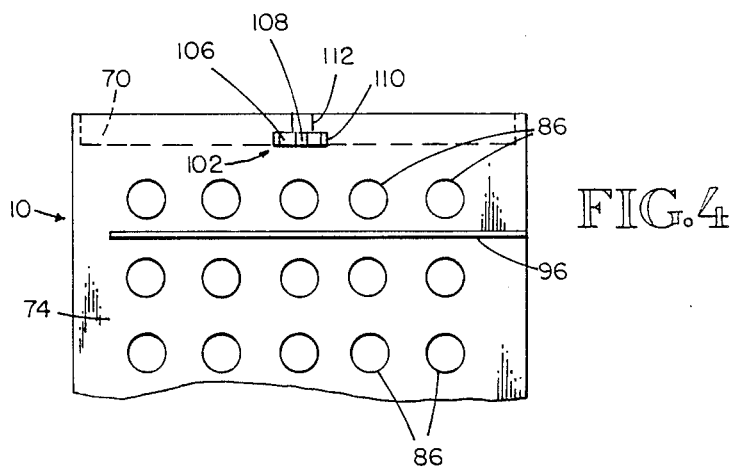
FIG. 4 is a bottom elevational view of one end portion of the first form of the sterilizing tray.

Each end door 70, 72 includes a pair of pivot pins 100 and a downwardly projecting necked tab 102, 104. As best seen in FIG. 4, each necked tab 102, 104 is offset from the side of its respective end door 70, 72 so that when end doors 70, 72 are closed and locked, the outer face of each end door 70, 72 will be flush with the ends of its respective tray side walls 74, 76.

Figure 5:
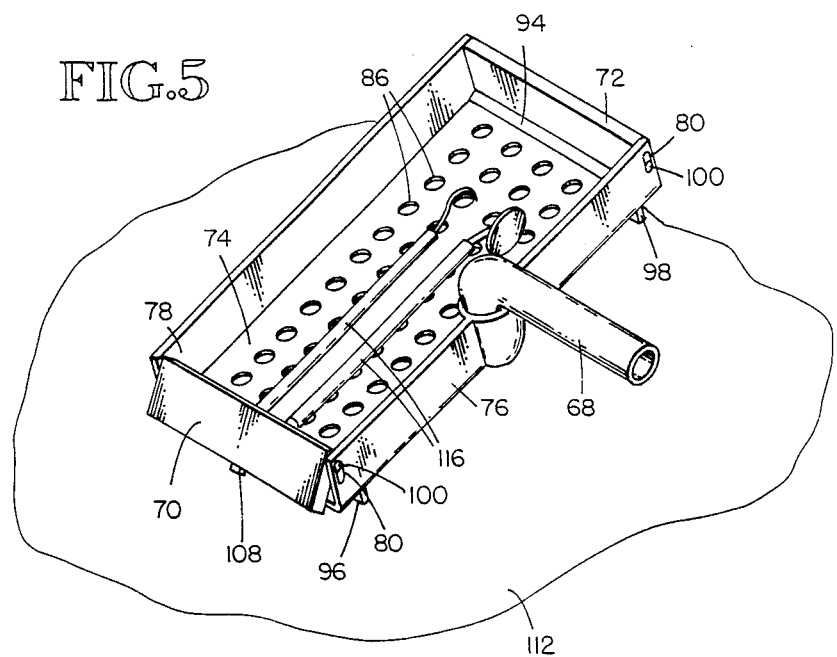
FIG. 5 is a perspective view showing the first form of the sterilizing tray being emptied.

As best seen in FIG. 5, each end door 70, 72 is pivotally mounted to tray body side walls 76, 78 by its respective pivot pins 100 which are received in their respective vertically elongated pivot slots 80 in tray body side walls 76, 78, as best seen in FIG. 5.

As best seen in FIG. 1, each necked tab 102, 104 comprises a wide latch tab 106, and a narrow release tab 108 which extends downwardly from its respective latch tab 106. Similarly, each necked slot 88, 90 comprises a wide latch slot 110 and a narrow release slot 112. Each latch slot 110 is sized to receive its corresponding latch tab 106. Each release slot 112 is sized to be narrower than its corresponding latch tab 106, and is also sized to be wider than its corresponding release tab 108.

As best seen in FIGS. 3 and 4, when tray end doors 70, 72 are closed, each latch tab 106 is received in its corresponding latch slot 110. This latches tray end doors 70, 72 securely shut, even if any items within tray 10 (such as dental instruments 116) push against the inside of tray end doors 70, 72.

As best seen in FIG. 3, the height of tray support legs 96, 98 is selected such that release tabs 108 are not accidentally pushed up and released when tray 10 is resting in a horizontal position on a flat support surface. Similarly, end ramps 92, 94 prevent dental instruments 116 within tray 10 from poking under the bottoms of end doors 70, 72, thereby preventing instruments 116 from accidentally opening end doors 70, 72.

In another form of sterilizing tray 10, the vertically elongated pivot slots 80 could be located in the lateral edges of end doors 70, 72, instead of in tray side walls 76, 78; and pivot pins 100 could be located on the inner faces of tray side walls 76, 78, instead of on the lateral edges of end doors 70, 72.

To use sterilizing tray 10 and sterilizing container 12, sterilizing container 10 is first filled with any suitable sterilizing fluid up to the bottoms of legs 60 on tray arms 16, 18. If desired, the date the sterilizing fluid was placed in sterilizing container 12 can then be conveniently recorded by sliding date slide 22 until the current date indicia 52 is seen through its date hole 54. It is desireable to do this because some sterilizing fluids have a useful lifespan of less than one month. Thus, by using date slide 22 to record when the sterilizing fluid was put in sterilizing container 12, it is easy to see if it is time to replace it with fresh sterilizing fluid.

Next, the objects to be sterilized, such as, by way of non-limiting example, dental instruments 116, are placed in sterilizing tray 10, after which sterilizing tray 10 is placed inside sterilizing container 12 on support legs 60 of tray arms 16, 18. Handle 68 is then rotated out of the way to a position such that it is over base 14 of sterilizing tray 10, so that cover 20 of sterilizing container 12 can be closed. When cover 20 is closed, tray arms 16, 18 automatically lower sterilizing tray 10, and its instruments 116 which it contains, down into the sterilizing fluid.

After instruments 116 have been sterilized, cover 20 of sterilizing tray 10 is raised, thereby causing tray arms 16, 18 to automatically elevate sterilizing tray 10, and its instruments 116, above the surface of the sterilizing fluid in sterilizing container 12. After the sterilizing fluid has drained out through drain holes 86 in sterilizing tray 10, sterilizing tray 10 is removed from sterilizing container 12 by use of its handle 68, which may be rotated so it is either pointing directly away from the center of sterilizing tray 10, as seen in FIG. 1, or which may be rotated so it is pointed directly in towards the center of sterilizing tray 10. In either position, handle 68 is releasably locked in place by its detent means in the manner previously described.

While instruments 116 are still in sterilizing tray 10, they and tray 10 are then thoroughly rinsed in hot water until any remaining sterilizing fluid is completely washed away.

Referring now to FIG. 5, in order to remove instruments 116 from sterilizing tray 10, tray end door 70 is first unlatched by tilting sterilizing tray 10 enough so that work surface 112 pushes end door release tab 108 upwardly enough so that latch tab 106 clears the top of its corresponding latch slot 110. Such upward movement of end door 70 and its latch tab 106 is permitted by the upward movement of end door pivot pins 100 in their vertically elongated pivot slots 80 in tray door side walls 76, 78.

Once tray end door 70 has been unlatched, the force of gravity urges dental instruments 116 against end door 70, causing it to open, thereby permitting instruments 116 to slide out of tray 10 onto work surface 112. Such movement of instruments 116 out of tray 10 may be assisted by moving tray 10 across work surface 112 in a direction opposite to the direction in which end door 70 has opened.

Work surface 112 will typically be a clean towel or other clean sheet material which has been placed on a table or counter so that instruments 116 are deposited on the clean sheet material when they exit tray 10, so they can be dried.

In order to close and latch tray end door 70, tray 10 is placed in a horizontal orientation while end door 70 is manually raised until its pivot pins 100 are at the tops of their vertically elongated pivot slots 80. At the same time, end door 70 is rotated on its pivot pins 100 until the bottom of end door 70 contacts its end ramp 92. End door 70 is then released, causing it to descend under the force of gravity until its latch tab 106 is received in its latch slot 110, thereby latching end door 70 securely closed.

The unlatching, opening, closing and latching of the other end door 72 of sterilizing tray 10 is done in a similar fashion.

Figure 6:
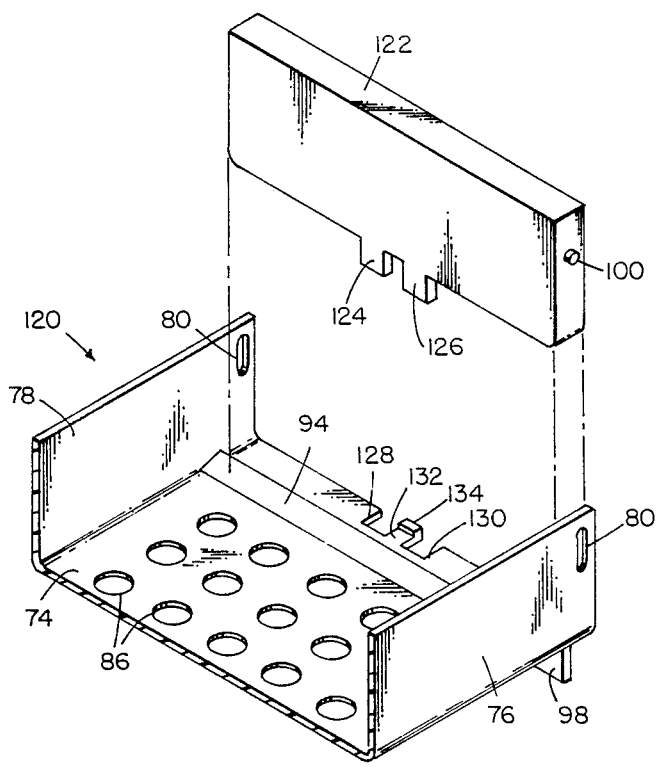
FIG. 6 is an exploded perspective view of one end portion of the second form of the sterilizing tray.

The second form 120 of the sterilizing tray of the present invention is illustrated in FIGS. 6–8. It is identical to sterilizing tray 10 illustrated in FIGS. 1-5 in materials, construction, operation and use, except for the few differences which are explained below. For clarity, parts of sterilizing tray 120 which are the same as those of sterilizing tray 10 have been given the same reference numerals.

Sterilizing tray 120 has a pair of end doors 122 which are each mounted with a pair of pivot pins 100. Pivot pins 100 are received in corresponding vertically elongated pivot slots 80 of side walls 76, 78. Extending downwardly from the bottom of each end door 122 is a pair of release tabs 124, 126.

As seen in FIGS. 7 and 8, when end doors 122 are latched closed, release legs 124, 126 are located in corresponding release slots 128, 130, respectively. At this time, as best seen in FIG. 7, latch tab 134 on latch arm 132 latches end door 122 securely shut, even if any items within tray 120 (such as dental instruments 116) push against the inside of tray end door 122.

As best seen in FIG. 7, the height of tray support leg 96 is selected such that release tabs 124, 126 of tray door 122 are not accidentally pushed up and released when tray 120 is resting in a horizontal position on a flat support surface. Similarly, end ramp 94 prevents dental instruments 116 within tray 120 from poking under the bottom of end door 122, thereby preventing instruments 116 from accidentally opening end door 122.

In order to remove instruments 116 from sterilizing tray 120, tray end door 122 is first unlatched by tilting sterilizing tray 120 enough so that work surface 112 pushes release tabs 124, 126 upwardly enough so that the bottom of end door 122 clears the top of latch tab 134 on latch arm 132. Such upward movement of end door 122 is permitted by the upward movement of end door pivot pins 100 in their vertically elongated pivot slots 80 in tray side walls 76, 78.

Once tray end door 122 has been unlatched, the force of gravity urges dental instruments 116 against end door 122, causing it to open, thereby permitting instruments 116 to slide out of sterilizing tray 120 onto work surface 112. Such movement of instruments 116 out of tray 120 may be assisted by moving tray 120 across work surface 112 in a direction opposite to the direction in which end door 122 has opened.

In order to close and latch tray end door 122 tray 120 is placed in a horizontal orientation while end door 122 is manually raised until its pivot pins 100 are at the tops of their vertically elongated pivot slots 80. At the same time, end door 122 is rotated on its pivot pins 100 until the bottom of end door 120 contacts its end ramp 94. End door 122 is then released, causing it to descend under the force of gravity until the bottom of end door 122 rests on latch arm 132, thereby latching end door 122 securely closed behind latch tab 134.

In another form of sterilizing tray 120, the vertically elongated pivot slots 80 could be located in the lateral edges of end doors 122, instead of in tray side walls 76, 78; and pivot pins 100 could be located on the inner faces of tray side walls 76, 78, instead of on the lateral edges of end doors 122.

The terms sterilizing tray 10, 120, sterilizing container 12, sterilizing fluid, sterilizing, and the like are used herein. However, it is to be expressly understood that all of the disclosures herein apply equally well to when instruments 116 are being disinfected or sanitized. Thus, the terms sterilizing tray 10, 120, sterilizing container 12, sterilizing fluid, sterilizing, and the like, as used herein are to be construed broadly enough to also cover disinfecting and sanitizing.

In view of the forgoing these, and further modifications, adaptations, and variations of the present invention will now be apparent to those skilled in the art to which it pertains, within the scope of the claims which follow. It is understood that the forgoing forms of the invention were shown strictly by way of non-limiting example.

What is claimed is:

1. A sterilizing tray for holding at least one object, wherein said sterilizing tray comprises: a base; a wall means for at least partially enclosing said base, wherein said wall means extend upwardly from said base, and wherein said wall means at least partially surround said base; at least one door means in said wall means, wherein said at least one door means is for selectively permitting the at least one object to exit said sterilizing tray, and wherein said at least one door means has a bottom; pivot means for pivotally mounting said at least one door means to said wall means; latch means, on at least one of said base and said at least one door means, said latch means for selectively latching said at least one door means closed; and release means, on at least one of said base and said at least one door means, said release means for selectively unlatching said at least one door means; wherein said sterilizing tray is adapted to be hand held by a user; and wherein at least a portion of said release means is sized to enable said portion of said release means to be urged against a work surface by said user sufficiently to unlatch said at least one door means, to permit said at least one object to exit said sterilizing tray through said at least one door means.

2. The sterilizing tray according to claim 1, wherein said at least one door means has a top portion; wherein said pivot means are at least partially located in said top portion of said at least one door means; and wherein said sterilizing tray is adapted to be tipped sufficiently while said at least one door means is unlatched, to permit the force of gravity to urge said at least one object against said at least one door means to at least assist opening said at least one door means on its said pivot means, and to permit the force of gravity to at least assist urging said at least one object to exit said sterilizing tray through said at least one door means.

3. The sterilizing tray according to claim 1, wherein said pivot means comprise: vertically elongated pivot slot means defined by one of said wall means and said at least one door means; and pivot pin means carried by the other of said wall means and said at least one door means; wherein said pivot slot means pivotally receive said pivot pin means.

4. The sterilizing tray according to claims 1, 2 or 3, wherein said latch means comprises a latch tab extending downwardly from the bottom of said at least one door means, and further comprises a latch slot in said base; wherein said latch slot and said latch tab are sized to enable said latch slot to selectively receive and retain said latch tab to latch said at least one door means; wherein said release means comprises a release tab extending downwardly from said latch tab, and further comprises a release slot in said base; wherein said release slot communicates with said latch slot; wherein said release slot is sized narrower than said latch tab; wherein said release slot is sized wider than said release tab; wherein said release tab is sized to enable said release tab to be urged against a work surface by said user sufficiently to cause said at least one door means to move upwardly on said pivot means a distance sufficient such that said latch tab is raised clear of said latch slot, to unlatch said at least one door means; and wherein said release tab is sized to enable said release tab to pass through said release slot to permit said at least one door means to open.

5. The sterilizing tray according to claim 4, wherein said sterilizing tray further comprises a safety ramp means which is located on said base adjacent said bottom of said at least one door means; wherein said safety ramp means is for preventing said at least one object from getting under said bottom of said at least one door means and accidentally unlatching said at least one door means.

6. The sterilizing tray according to claim 4, wherein said sterilizing tray further comprises foot means on said base; and wherein said foot means are for preventing said work surface from urging said release tab upwardly a distance sufficient to unlatch said at least one door means when said sterilizing tray is placed on said work surface horizontally.

7. The sterilizing tray according to claims 2, 3 or 4, wherein said latch means comprises a latch tab on said base to latch said at least one door means closed; wherein said release means comprises at least one release tab extending downwardly from the bottom of said at least one door means, and at least one corresponding release slot in said base; wherein said at least one release slot is sized wider than said at least one release tab; wherein said at least one release tab is sized to enable said at least one release tab to be urged against a work surface by said user sufficiently to cause said at least one door means to move upwardly on said pivot means a distance sufficient such that said bottom of said at least one door means is raised clear of said latch tab, to unlatch said at least one door means; and wherein said at least one release tab is sized to enable said at least one release tab to pass through said at least one release slot to permit said at least one door means to open.

8. The sterilizing tray according to claim 7, wherein said sterilizing tray further comprises a safety ramp means which is located on said base adjacent said bottom of said at least one door means; wherein said safety ramp means is for preventing said at least one object from getting under said bottom of said at least one door means and accidentally unlatching said at least one door means.

9. The sterilizing tray according to claim 7, wherein said sterilizing tray further comprises foot means on said base; and wherein said foot means are for preventing said work surface from urging said at least one release tab upwardly a distance sufficient to unlatch said at least one door means when said sterilizing tray is placed on said work surface horizontally.

* * * * *